US010151732B1

(12) United States Patent
Moorman et al.

(10) Patent No.: US 10,151,732 B1
(45) Date of Patent: Dec. 11, 2018

(54) SEALED MICRO GAS CHROMATOGRAPHY COLUMNS AND METHODS THEREOF

(71) Applicant: National Technology & Engineering Solutions of Sandia, LLC, Albuquerque, NM (US)

(72) Inventors: Matthew W. Moorman, Albuquerque, NM (US); Ronald P. Manginell, Albuquerque, NM (US); John Moses Anderson, Albuquerque, NM (US); Robert J. Simonson, Cedar Crest, NM (US); Douglas Read, Bosque Farms, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 387 days.

(21) Appl. No.: 14/992,871

(22) Filed: Jan. 11, 2016

Related U.S. Application Data

(60) Provisional application No. 62/105,019, filed on Jan. 19, 2015.

(51) Int. Cl.
*G01N 30/60* (2006.01)

(52) U.S. Cl.
CPC ....... *G01N 30/606* (2013.01); *G01N 30/6095* (2013.01)

(58) Field of Classification Search
CPC ............. G01N 30/606; G01N 30/6095; G01N 2030/6056
See application file for complete search history.

(56) References Cited

U.S. PATENT DOCUMENTS

| | | | |
|---|---|---|---|
| 5,583,281 A * | 12/1996 | Yu | G01N 30/20 73/23.42 |
| 5,820,922 A | 10/1998 | Ricco et al. | |
| 5,834,627 A | 11/1998 | Ricco et al. | |
| 6,096,656 A | 8/2000 | Matzke et al. | |
| 6,171,378 B1 | 1/2001 | Manginell et al. | |
| 6,224,728 B1 | 5/2001 | Oborny et al. | |
| 6,527,835 B1 | 3/2003 | Manginell et al. | |
| 6,617,591 B1 | 9/2003 | Simonson et al. | |
| 6,666,907 B1 | 12/2003 | Manginell et al. | |
| 6,699,392 B1 | 3/2004 | Manginell et al. | |
| 6,706,091 B1 | 3/2004 | Robinson et al. | |
| 6,772,513 B1 | 8/2004 | Frye-Mason et al. | |
| 6,786,716 B1 | 9/2004 | Gardner et al. | |
| 6,902,701 B1 | 6/2005 | Hughes et al. | |

(Continued)

OTHER PUBLICATIONS

Lewis et al., "Recent Advancements in the Gas-Phase MicroChemLab", IEEE Sensors Journal, vol. 6, No. 3 (2006), pp. 784-795.

(Continued)

*Primary Examiner* — Robert Clemente
(74) *Attorney, Agent, or Firm* — Helen S. Baca

(57) ABSTRACT

The present application relates to microfabricated columns having a sealed flow channel. In particular, the channel is sealed during dicing, thereby preventing debris from accumulating within channels. In use, the seal is ruptured mechanically to connect one or more fluidic connections, which deliver analytes to the flow channel. Additional details are provided for making and using sealed columns.

30 Claims, 6 Drawing Sheets

(56) References Cited

U.S. PATENT DOCUMENTS

| | | |
|---|---|---|
| 6,930,051 B1 | 8/2005 | Manginell et al. |
| 7,078,237 B1 | 7/2006 | Mowry et al. |
| 7,105,098 B1 | 9/2006 | Shul et al. |
| 7,118,712 B1 | 10/2006 | Manginell et al. |
| 7,168,298 B1 | 1/2007 | Manginell et al. |
| 7,399,449 B1 | 7/2008 | Oborny et al. |
| 7,422,724 B1 | 9/2008 | Manginell et al. |
| 7,708,943 B1 | 5/2010 | Robinson et al. |
| 7,727,314 B1 | 6/2010 | Manginell et al. |
| 7,799,280 B1 | 9/2010 | Manginell et al. |
| 7,913,534 B1 | 3/2011 | Robinson et al. |
| 8,123,841 B2 | 2/2012 | Masel et al. |
| 8,298,488 B1 | 10/2012 | Lewis et al. |
| 8,486,710 B2 | 7/2013 | Antel et al. |
| 8,562,878 B1 | 10/2013 | Martin et al. |
| 8,736,000 B1 | 5/2014 | Manginell et al. |
| 8,846,406 B1 | 9/2014 | Martin et al. |
| 9,472,689 B1 | 10/2016 | Elizondo-Decanini et al. |
| 9,995,411 B1 | 6/2018 | Moorman et al. |
| 2014/0138351 A1* | 5/2014 | Mancarella ........ G01N 30/6095 216/37 |
| 2014/0165841 A1* | 6/2014 | Otsuka ............... G01N 30/6095 96/101 |

OTHER PUBLICATIONS

Matze et al., "Microfabricated Silicon Gas Chromatographic Micro-Channels: Fabrication and Performance", SPIE Conference on Micromachining and Microfabrication Process Technology IV (Sep. 1998), SPIE vol. 3511, pp. 262-268.

U.S. Appl. No. 14/538,096, filed Nov. 11, 2014, Polsky et al.

U.S. Appl. No. 14/945,274, filed Nov. 18, 2015, Moorman et al.

U.S. Appl. No. 14/992,855, filed Jan. 11, 2016, Manginell et al.

U.S. Appl. No. 15/237,193, filed Aug. 15, 2016, Miller et al.

Cortes HJ et al., "Comprehensive two dimensional gas chromatography review," *J. Sep. Sci.* 2009;32:883-904.

Frye-Mason G et al., "Hand-held miniature chemical analysis system (μChemLab) for detection of trace concentrations of gas phase analytes," *Sandia Report No. SAND2000-1480A*, 2000 (4 pp.).

Galambos P et al., "Active MEMS valves for flow control in a high-pressure micro-gas-analyzer," *J. Microelectromech. Sys.* Oct. 2011;20(5):1150-62.

Kim BC et al., "Fracture-based micro- and nanofabrication for biological applications," *Biomater. Sci.* 2014;2:288-96.

Manginell RP et al., "A monolithically-integrated μGC chemical sensor system," *Sensors* 2011;11:6517-32.

Manginell RP et al., "Mass-sensitive microfabricated chemical preconcentrator," *J. Microelectromech. Sys.* Dec. 2008;17(6):1396-407.

Nam KH et al., "Patterning by controlled cracking," *Nature* May 2012;485:221-4.

Seeley JV et al., "Multidimensional gas chromatography: fundamental advances and new applications," *Anal. Chem.* 2013;85:557-78.

Wang D et al., "Sol-gel column technology for single-step deactivation, coating, and stationary-phase immobilization in high-resolution capillary gas chromatography," *Anal. Chem.* 1997;69:4566-76.

Yang C et al., "On the residual stress and fracture strength of crystalline silicon wafers," *Appl. Phys. Lett.* 2013;102:021909 (5 pp.).

* cited by examiner

US 10,151,732 B1

SEALED MICRO GAS CHROMATOGRAPHY COLUMNS AND METHODS THEREOF

CROSS-REFERENCE TO RELATED APPLICATION

This application claims priority to U.S. Provisional Patent Application No. 62/105,019, filed on Jan. 19, 2015 under the title, "SEALED MICRO GAS CHROMATOGRAPHY COLUMNS AND METHODS THEREOF," the entirety of which is incorporated herein by reference.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD

The present application relates to a microfabricated column having a sealed flow channel. In use, the seal is ruptured mechanically to connect one or more fluidic connections, which deliver analytes to the flow channel. Additional details are provided for making and using sealed columns.

BACKGROUND

Gas chromatography (GC) is a widely employed technique for separating target analytes and markers. In particular, microfabricated gas chromatograph (μGC) columns can provide a separation platform for use in miniaturized, portable detectors. In addition, such μGC columns typically have high surface-to-volume ratios, which can potentially increase separation efficiency. Despite these benefits, a pervasive problem with μGC columns includes channel blockage or contamination due to debris accumulation. In particular, to withstand high temperature applications, μGC columns are formed from durable materials (e.g., glass or silicon) that require dicing, which generally employs agents such as lubricants and/or coolants. Use of these agents can introduce debris and contaminants into microstructures in the μGC column, and such debris is difficult to remove in such microstructures. Thus, new structures and devices are needed to address these difficulties.

SUMMARY

The present application relates to a microfabricated gas chromatograph (μGC) design that solves an enduring problem with μGCs constructed using conventional silicon microfabrication techniques. Conventional μGC fabrication processes generally include use of a dicing step, which introduces contaminants into high-aspect ratio columns that are desired for optimal separation. The presence of these contaminants reduces column performance and manufacturability by interfering with column flow and with the deposition of stationary phase chemistries. While alternate techniques to remove individual die from the wafer exist, such as laser cutting and scribe and break processes, the thickness of the glass-silicon stack for modern μGC devices (~1.5 mm) precludes their use.

Here, we describe thin membrane sealing structures into the μGC design. The temporary membrane structures (e.g., having a dimension of about 100 μm) are located at the inlets of the μGC columns. These structures seal the channels and fluid connections, preventing water and dicing debris from entering the μGC. These seals are only broken in a clean environment immediately before fluidic connections are made to the chip, leaving a pristine column surface for deposition of the μGC stationary phase chemistries. After dicing and cleaning of the chip exterior, a probe tip or other mechanical tool is used to rupture the membrane, allowing the μGC fluidic connections to be made. The membrane rupture produces a minor amount of silicon particulate in the fluidic connectors, but these loose particles are easily removed via a vacuum line. Exemplary advantages include a simple process that keeps the μGC free of debris and contaminants during the dicing process, as well as an extended storage time for sealed diced columns without fear of atmospheric contaminants entering the channels. Additional details follow.

Definitions

As used herein, the term "about" means+/−10% of any recited value. As used herein, this term modifies any recited value, range of values, or endpoints of one or more ranges.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

By "microfluidic" or "micro" is meant having at least one dimension that is less than 1 mm. For instance, a microfluidic structure (e.g., any structure described herein) can have a length, width, height, cross-sectional dimension, circumference, radius (e.g., external or internal radius), or diameter that is less than 1 mm.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the application will be apparent from the following description and the claims.

BRIEF DESCRIPTION OF THE DRAWINGS

FIG. 2A provides schematics of a device 200 including a sealed μGC column in a plan view. FIG. 2B provides schematics of a device 200 including a sealed μGC column in a cross-sectional view. FIG. 2C provides schematics of a device 200 including a sealed μGC column in an end view.

FIG. 3A provides a non-limiting method of fabricating a column. FIG. 3B provides schematics of a plan view of an exemplary sealed μGC column 300. FIG. 3C provides schematics of a cross-sectional view along line 3C-3C' of an exemplary sealed μGC column 300. FIG. 3D provides schematics of a cross-sectional view along line 3D-3D' of an exemplary sealed μGC column 300. FIG. 3E provides schematics of an end view of an exemplary sealed μGC column 300. FIG. 3F provides schematics of a cross-sectional view along line 3F-3F' of an exemplary sealed μGC column 300.

FIG. 4A provides a schematic of a plan view of an exemplary sealed μGC column having a flow channel 420 and a heating element 470. FIG. 4B provides a schematic of a close-up view of an exemplary sealed μGC column having a flow channel 420 and a heating element 470.

FIG. 5A provides scanning electron micrographs of μGC columns formed without the sealed structure, showing the presence of contaminants. FIG. 5B provides scanning electron micrographs of μGC columns formed with the sealed structure.

DETAILED DESCRIPTION

The present application relates to sealed μGC columns, as well as uses thereof and methods of making such columns. In general, the sealed μGC column includes a flow channel and one or more seals installed during the dicing stage of the fabricating the column. Fabrication steps typically include forming a flow channel (or a portion thereof) in a substrate, aligning the substrate with a lid, bonding the substrate and the lid to form a stack, and then dicing the stack to form a die. In some embodiments, the lid can include one or more structures (e.g., a proximal channel, a distal channel, or a portion of the flow channel, in which the channel portion in the substrate and the channel portion in the lid are aligned to form a complete flow channel). In particular embodiments, the seal(s) are provided in the dicing step.

Figure 1:
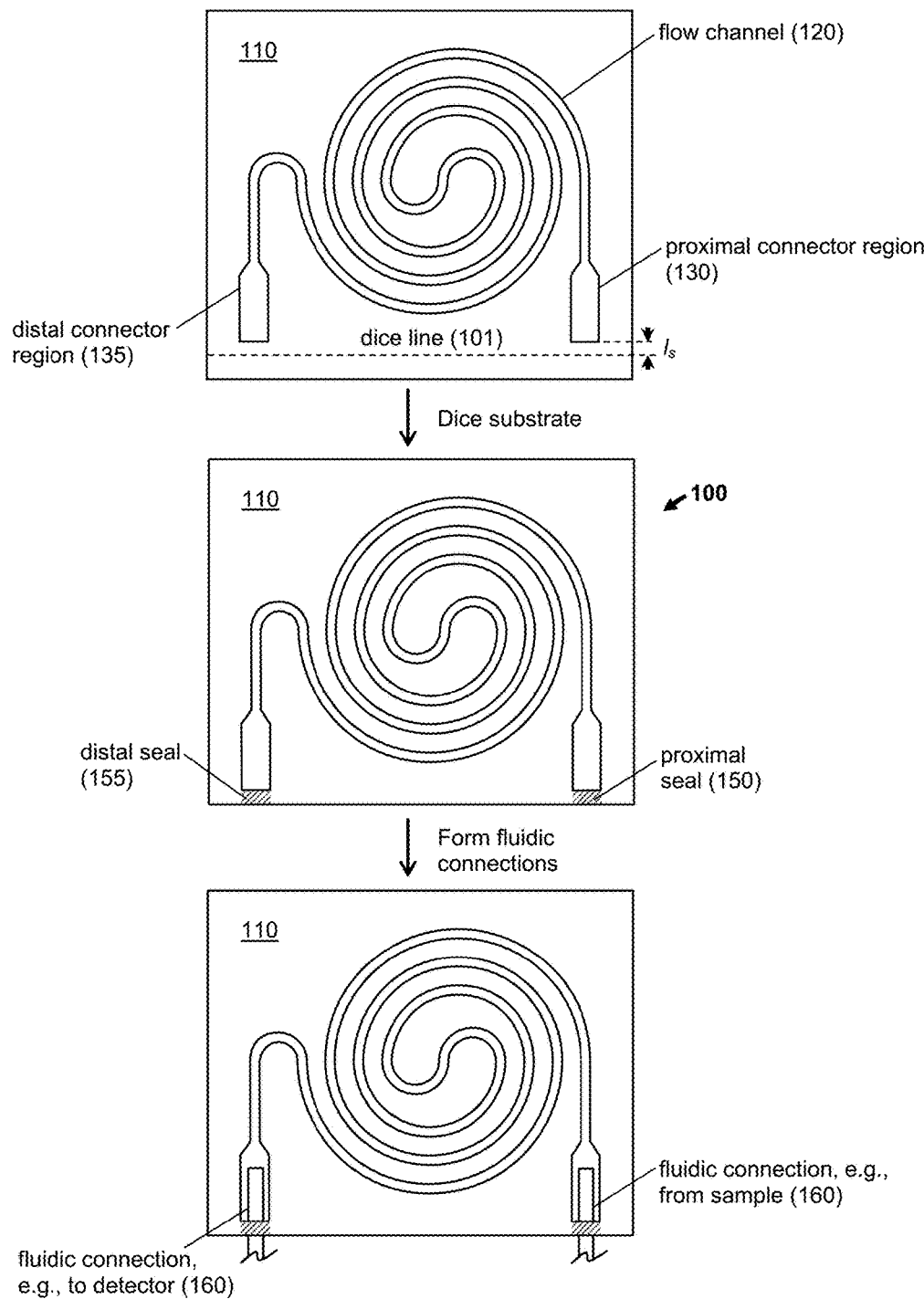
FIG. 1 is a schematic of an exemplary sealed μGC column 100 and a non-limiting method of fabricating such a column.
Figure 3A:
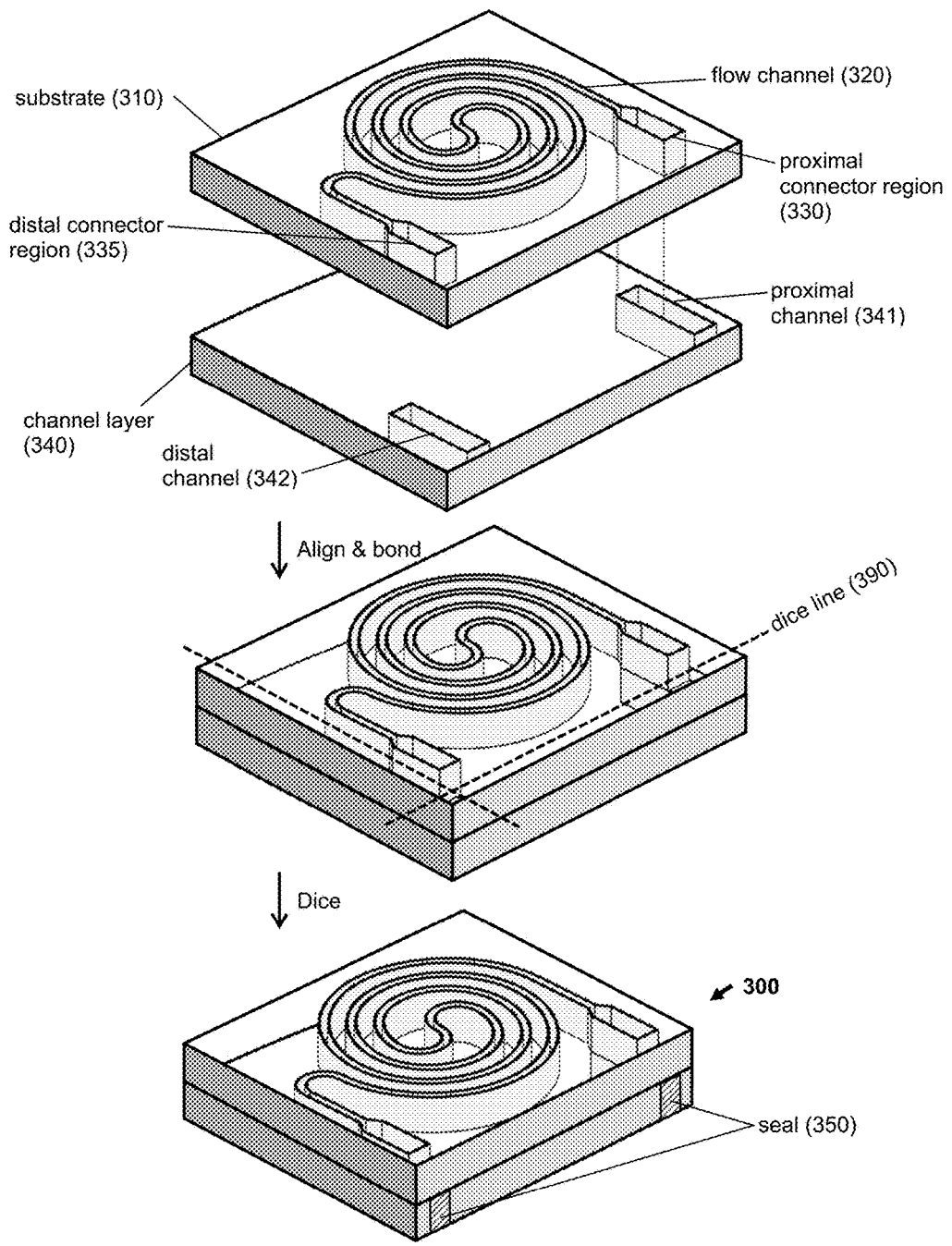
FIG. 3A-3F provides schematics of an exemplary sealed μGC column 300, including (A) a non-limiting method of fabricating such a column and various views, such as (B) a plan view, (C) a cross-sectional view along line 3C-3C', (D) a cross-sectional view along line 3D-3D', (E) an end view, and (F) a cross-sectional view along line 3F-3F'.

FIG. 1 provides a schematic of an exemplary method to install a seal during the dicing step. As can be seen, the substrate 110 includes a flow channel 120. The substrate can include any useful material (e.g., any described herein). Furthermore, the flow channel can be configured within the substrate in any useful way. For instance, the flow channel can be embedded entirely within the substrate (e.g., by employing a first substrate including a top portion of the flow channel, providing a second substrate including a bottom portion of the flow channel, and aligning the first and second substrates to form a complete flow channel including the top and bottom portions). Alternatively, the flow channel can be formed as a recessed portion on a bottom surface of the substrate. To enclose the flow channel, the bottom surface of the substrate can be bonded to another substrate, channel layer, or lid to form a surface of the flow channel (e.g., as seen in FIG. 3C, which provides three surfaces of a flow channel defined as a recessed portion in the substrate 310 and the fourth surface of the flow channel, as defined by a portion of the channel layer/lid 360).

The flow channel can be in fluid communication with any other useful channel, chamber, or connection channel. For instance, as shown in FIG. 1, the flow channel 120 can be in fluidic communication with a proximal connector region 130 and a distal connector region 135. In particular embodiments, the connector region(s) facilitate connection of one or more capillaries or tubing to introduce a sample into the μGC column and/or to deliver a separated sample from the μGC column to a detector. In some embodiments, the connector region generally is an enlarged or widening channel that connects a flow channel (generally having a micron-sized dimension) to a tubing (generally having a millimeter-sized dimension).

To form multiple μGC columns, a plurality of individual flow channels is generally etched on a wafer. After forming flow channels in a substrate, the substrate is generally bonded to a further substrate, a channel layer, and/or a lid, thereby forming a stack. Then, the dicing step cuts and separates each flow channel into individual dies or devices, thereby forming a plurality of dies. Typically, dicing includes use of a rotating saw in the presence of a lubricant (e.g., to facilitate dicing) and/or a coolant (e.g., to prevent damage from heat generated by the rotating saw), which can be beneficial for dicing. However, when the flow channel is diced, thereby providing a fluidic connection between the flow channel and the external environment, such lubricants and coolants (including any debris arising from cutting the stack) can be introduced into the flow channel. To install a seal during the dicing step (FIG. 1), the user ensures that the dicing line 101 is located a length $l_s$ from the edge of the stack. Then, dicing forms the sealed μGC column 100 having a proximal seal 150 disposed in the proximal connector region 130, as well as a distal seal 155 disposed in the distal connector region 135. Prior to use, fluidic connections 160 can be formed (e.g., from a sample into the proximal connector region 130 or to the detector from the distal connector region 135).

Figure 4A:
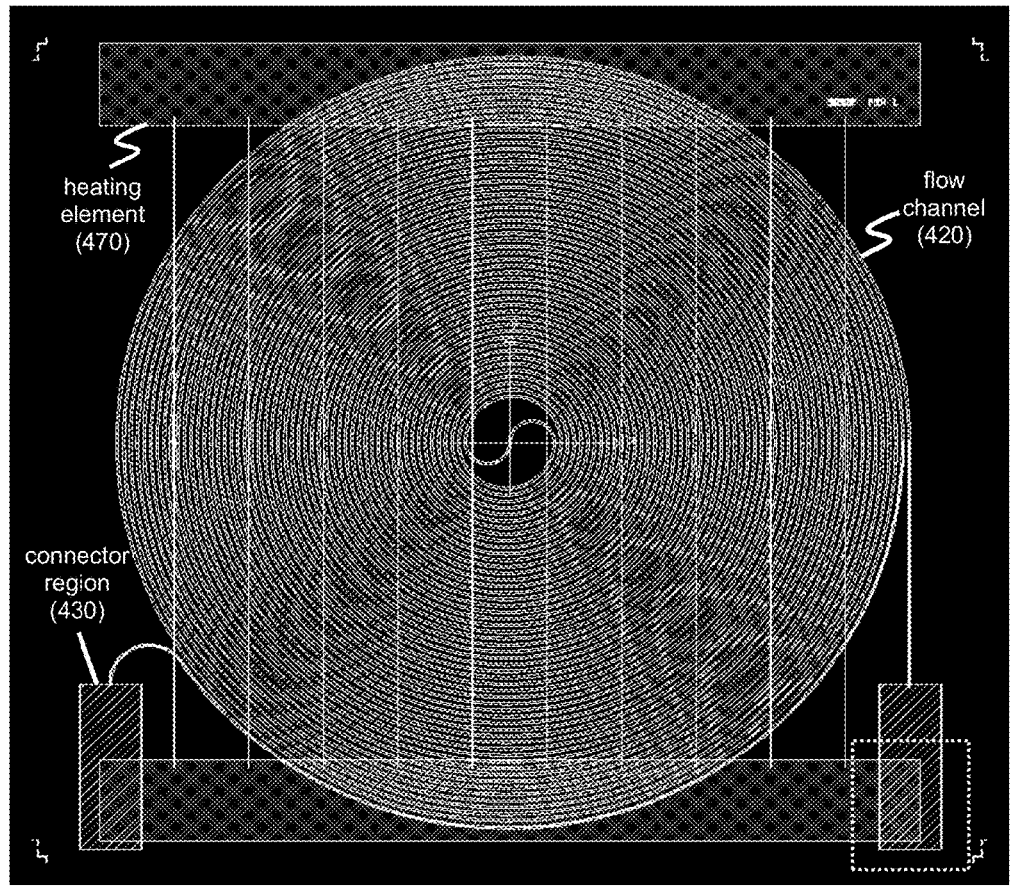
FIG. 4A-4B provides a schematic of an exemplary sealed μGC column having a flow channel 420 and a heating element 470 in (A) a plan view and (B) a close-up view of an area in FIG. 4A (provided as a dashed rectangle).
Figure 4B:
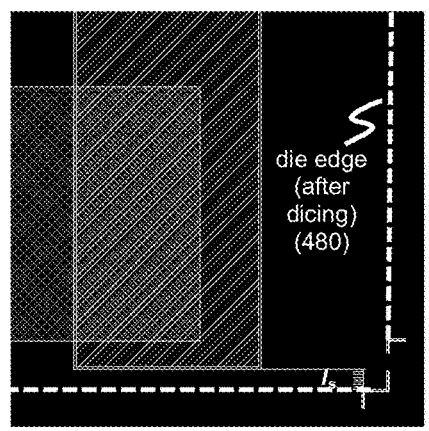

FIG. 4A-4B provides the μGC column prior to dicing. For instance, the column can include a flow channel 420 and a connector region 430, where the location of the heating element 470 is provided for reference. The dice edge 480 (after dicing) can be located a distance $l_s$ from an edge of the connector region 430 (FIG. 4B).

The length $l_s$ provides a length dimension from the seal. Prior to use, a puncturing tool is employed to mechanically rupture the seal. Thus, $l_s$ is of a sufficient length to enclose the flow channel, and yet thin enough to ensure rupturing without requiring significant force. In some embodiments, $l_s$ is of from about 10 μm to about 500 μm. Methods for measuring fracture and rupture strength of materials are described in Yang C et al., "On the residual stress and fracture strength of crystalline silicon wafers," *Appl. Phys. Lett.* 2013; 102:021909 (5 pp.); Kim B C et al., "Fracture-based micro- and nanofabrication for biological applications," *Biomater. Sci.* 2014; 2:288-96; and Nam K H et al., "Patterning by controlled cracking," *Nature* 2012 May; 485:221-4, each of which is incorporated herein by reference in its entirety.

Figure 2A:
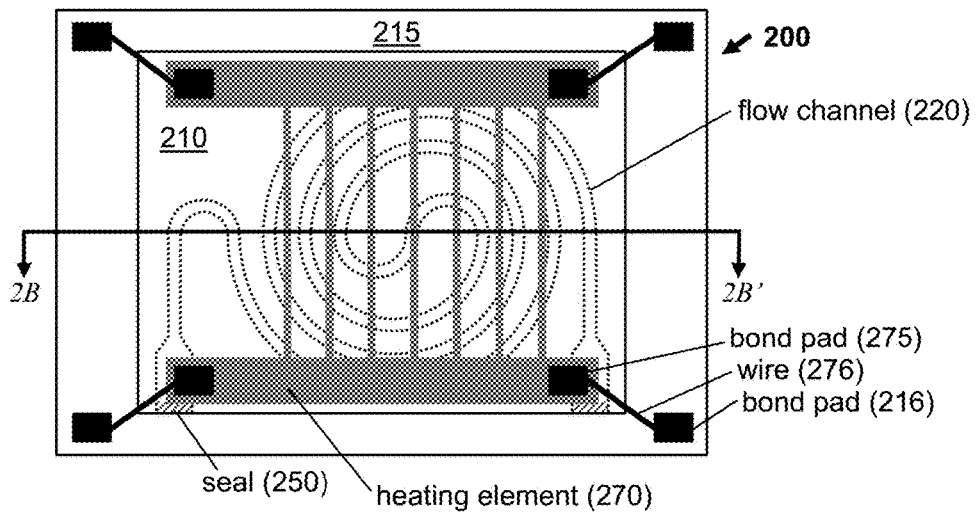
FIG. 2A-2C provides schematics of a device 200 including a sealed μGC column in (A) a plan view, (B) a cross-sectional view along line 2B-2B', and (C) an end view.
Figure 2B:
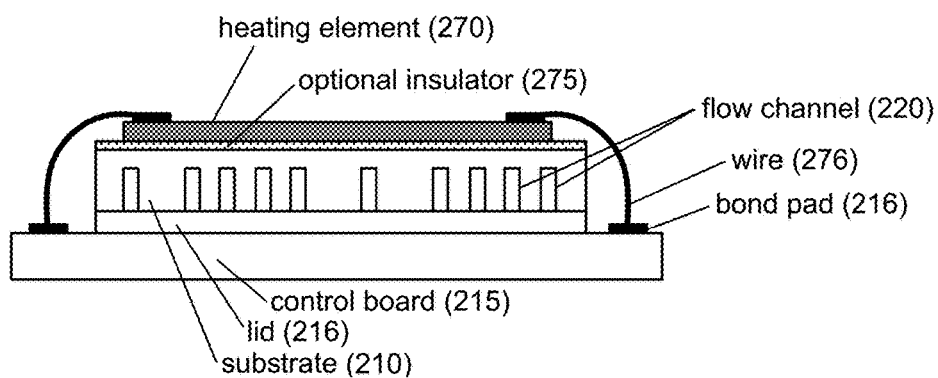
Figure 2C:
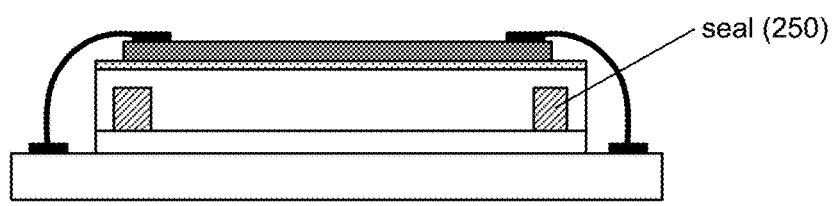

The sealed μGC column can be employed in any useful device. For instance, as shown in FIG. 2A-2C, the device 200 can include the sealed μGC column disposed in the substrate 210. In this exemplary column, a lid 216 is bonded to the bottom surface of the substrate 210, thereby enclosing the flow channel 220.

As shown in FIG. 2A, a heating element 270 is disposed above the sealed μGC column, and a control board 215 is located beneath the sealed μGC column. Electrical connections are formed between the heating element 270 and the control board 215 by way of bond pads 216, 275 and wires 276. Such bond pads and wires can be formed from any useful material (e.g., a conductive metal, such as any described herein). As shown in FIGS. 2A and 2C, the seals 250 for the μGC column are located on the edge of the stack and unobstructed by the heating element or control board, thereby facilitating access to these seals for rupturing prior to use.

The heating element 270 can include any other components useful for its operation, such as a control board 215 to provide power and signals to the heating element, as well as an optional insulator 275 to efficiently retain heat within the μGC column (FIG. 2B). In particular uses, heating can improve separation efficiency.

The sealed μGC column can include the use of a substrate with a lid (e.g., as in FIG. 2B) or the use of a substrate with a channel layer. As seen in FIG. 3A, the channel layer 340 can also be used to provide channels that serve as inlets and outlets, as well as provide a fluidic connection to external tubing or capillaries. Any useful method can be employed to form this column. For instance, the substrate 310 can include a flow channel 320, a proximal connector region 330 in fluidic communication with the flow channel 320, and a distal connector region 335 in fluidic communication with the flow channel 320. In some embodiments, the connector regions have a widened portion, as compared to the flow channel. In yet other embodiments, the connector regions have dimensions commensurate (e.g., width or height) with the flow channel. The channel layer 340 can include a proximal channel 341 and a distal channel 342.

Then, the substrate 310 is aligned to the channel layer 340 and subsequently bonded together to form a stack. Next, the stack is diced along the dice line 390 to provide a sealed μGC column 300 having seals 350 along an edge of the stack.

The completed sealed μGC column generally includes a flow channel, a proximal connector region, a distal connector region, and seals (e.g., disposed in the connector regions). As shown in FIG. 3B-3F, the column can also include proximal and distal channels, in which case the seals can be disposed in the channels. For instance, the sealed μGC column 300 can include a flow channel 320, a proximal connector region 330, and a proximal channel 341 in fluidic communication with the flow channel 320 and the proximal connector region 330. Whereas the flow channel 320 and the proximal connector region 330 are located in the substrate 310, the proximal connector region 330 is located in the lid/channel layer 360. The seal 350 is configured to be located on the edge of the stack (FIG. 3E) and can be located in the proximal channel 341 (FIG. 3F).

Dimensions

Figure 3B:
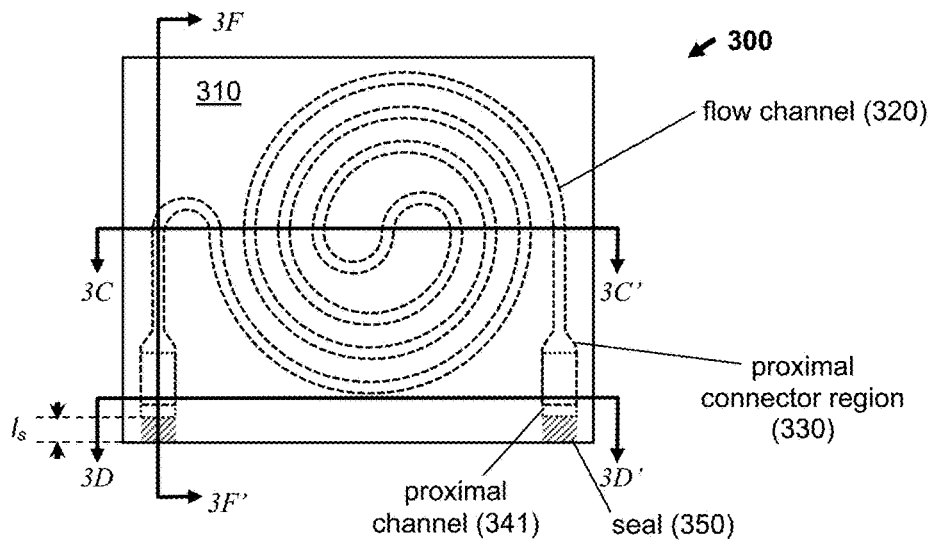
Figure 3C:
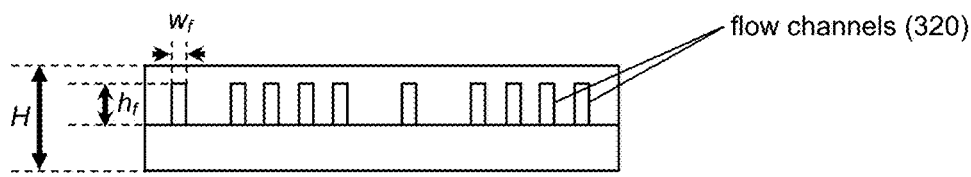
Figure 3D:
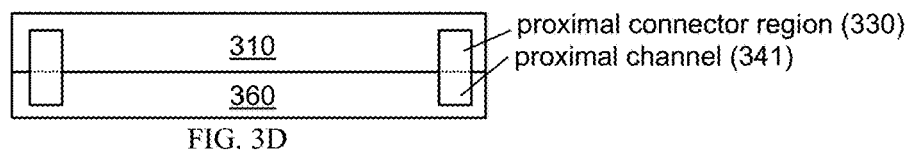
Figure 3E:
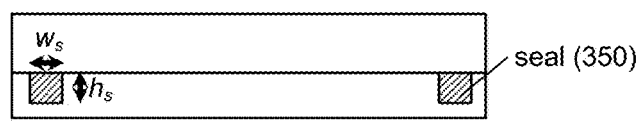
Figure 3F:
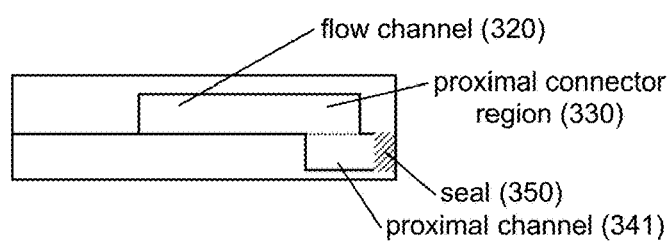

The structures of the μGC column can have any useful dimensions, including the height of the stack H, the length of the flow channel $l_f$, the width of the flow channel $w_f$, the height of the flow channel $h_f$, the length of the seal $l_s$, the width of the seal $w_s$, and the height of the seal $h_s$ (FIGS. 3B, 3C, and 3E). In one embodiment, the flow channel is a microchannel.

The flow channel, connector regions, and seals can have any useful cross-sectional shape and dimension. Exemplary cross-sections include square, rectangle, circular, oval, semicircular, etc. shapes with any useful dimension, such as a width or height (e.g., a dimension on the same axis as $w_f$, $h_f$, $w_s$, or $h_s$) of from about 10 μm to 800 μm (e.g., a width of about 10 μm to 200 μm, and a height of about 100 μm to 800 μm). In some instances, the height-to-width ratio of the flow channel is greater than 25:1, 10:1, 5:1, or 2:1. In yet other instances, the flow channel has a length of about 10 cm to about 1 m. The flow channel can have any useful arrangement (e.g., to maximize channel length on a particular area of the substrate), such as a serpentine, circular, linear, or spiral arrangement, as well as any described in U.S. Pat. No. 8,123,841, which is incorporated herein by reference in its entirety.

The seal can have any useful dimension configured to be ruptured mechanically (e.g., ruptured with a mechanical force in the direction of the axis for $l_s$, as shown in FIG. 3B), as well as maintain its integrity during the dicing process. In some embodiments, $l_s$ is of from about 10 μm to about 500 μm (e.g., from about 10 μm to 100 μm, 10 μm to 250 μm, 10 μm to 400 μm, 25 μm to 100 μm, 25 μm to 250 μm, 25 μm to 400 μm, 25 μm to 500 μm, 50 μm to 100 μm, 50 μm to 250 μm, 50 μm to 400 μm, 50 μm to 500 μm, 75 μm to 100 μm, 75 μm to 250 μm, 75 μm to 400 μm, 75 μm to 500 μm, 100 μm to 250 μm, 100 μm to 400 μm, 150 μm to 250 μm, 150 μm to 400 μm, 150 μm to 500 μm, 200 μm to 250 μm, 200 μm to 400 μm, 250 μm to 500 μm, 300 μm to 400 μm, or 300 μm to 500 μm).

The present application is particularly useful when the height H of the stack is such that other non-dicing techniques (e.g., laser scribing) are no longer effective. Exemplary values for H include more than about 1 mm, e.g., of from about 1 mm to about 5 mm. In some embodiments, the stack includes a substrate (e.g., about 500 μm or less or about 250 μm or less) and lid (e.g., less than about 1 mm, about 500 μm or less, or about 250 μm or less).

Stationary Phases for Flow Channel

The column can include one or more phases or coatings formed from any useful material. For instance, the flow channel can include stationary phase to facilitate analyte separation. A stationary phase can be employed to coat a surface of the flow channel or to pack an internal volume of the flow channel.

Exemplary stationary phases include a polar stationary phase, a non-polar stationary phase, a molecular sieve, an alumina, a silica, as well as particle, gel, sol-gel, polymer, and solution forms of any of these.

Exemplary stationary phases include poly(dimethylsiloxane) (PDMS), a mixture or copolymer of phenylmethylsiloxane and PDMS, phenylmethylsiloxane, a mixture of copolymer of phenylmethylsiloxane and diphenylsiloxane, a mixture or copolymer of diphenylsiloxane and PDMS, trifluoropropylmethylsiloxane, a mixture or copolymer of cyanopropylmethylsiloxane and PDMS, a mixture or copolymer of cyanopropylphenylsiloxane and PDMS, dicyanoalkylsilixane, polyethylene glycol (PEG), polyglycol-nitroterephthalic, beta-cyclodextrin, molecular sieve zeolite, aluminum oxide, polystyrene-divinylbenzene, and/or diethyleneglycol succinate.

Stationary phases and coatings can be deposited within the flow channel or on the surface of the flow channel in any useful manner. In one non-limiting approach, a plug of the stationary phase material is transported through the flow channel (e.g., with pressurized gas). In a second non-limiting approach, the flow channel is first filled with the stationary phase material, and then the excess is removed by applying a vacuum to the end of the channel. Other exemplary methodologies include use of a stationary phase with a catalyst (e.g., azodiisobutyronitrile) on an activated channel surface (e.g., by oxidizing the surface of the flow channel or silanizing the channel surface with an activated silane, such as a halo-, hydroxyl-, or vinyl-terminated silane). Another methodology includes use of a sol-gel process to passivate and coat a channel with the stationary phase, in which the sol solution includes an alkoxide-based precursor (e.g., methyltrimethoxysilane or tetramethoxysilane), a hydroxy-terminated stationary phase (e.g., PDMS), a surface derivatizing agent, and a catalyst (e.g., trifluoroacetic acid). Yet another methodology includes use of a primer to enhance wettability of the channel surface and to covalently link the stationary phase to the microfabricated column or flow channel. Additional methodologies are described in Frye-Mason G et al., "Hand-held miniature chemical analysis system (μChemLab) for detection of trace concentrations of gas phase analytes," *Sandia Report No. SAND*2000-1480*A*, 2000 (4 pp.); Matzke C M et al., "Microfabricated silicon gas chromatographic micro-channels: fabrication and performance," *Proc. SPIE* 1998; 3511:262-8; Wang D et al., "Sol-gel column technology for single-step deactivation, coating, and stationary-phase immobilization in high-resolution capillary gas chromatography," *Anal. Chem.* 1997; 69:4566-76; and U.S. Pat. No. 8,123,841, each of which is incorporated herein by reference in its entirety.

Uses

The sealed μGC column herein can be employed for any useful purpose. For instance, the column can be used to separate and/or to facilitate detection of any useful analyte (e.g., a volatile analyte). Exemplary analytes include one or more of the following: light gases (e.g., hydrogen, methane, carbon dioxide, or carbon monoxide, or any greenhouse gas (GHG)); volatile organic compounds (VOCs, e.g., from any source, such as microorganisms, pathogens, humans, toxic industrial chemicals (TICs), solvents, fixed/permanent gases, explosives, GHG, water contaminants, and/or chemical and biological warfare agents (CWAs and BWAs)), such as acids (e.g., isovaleric acid), aldehydes (e.g., acetaldehyde or 3-methylbutanal), ketones (e.g., acetoin or 2-nonanone), hydrocarbons (e.g., 2-butene or 1,10-undecadiene), alcohols (e.g., 2-methyl-1-propanol, 2-butanol), phosphonates (e.g., dimethyl methyl phosphonate, diethyl methyl phosphonate, or diisopropyl methyl phosphonate), esters (e.g., ethyl formate or methyl 2-methylbutyrate), including volatile nitrogen compounds (e.g., methylpyrrole), and volatile sulfur compounds (e.g., dimethylsulfide); semi-volatile organic compounds; human-specific volatile signals (e.g., hexenoic acid, such as 3-methyl-2-hexenoic acid or (E)-3-methyl-2-hexenoic acid; volatile signatures of pathogens (e.g., bacteria, food pathogens, or biological warfare agents, such as *Salmonella*, *Staphylococcus* (e.g., *S. aureus*), *Bacillus*, *Mycobacteria* (e.g., *M. bovis* or *M. tuberculosis*), *Pseudomonas* (e.g., *P. aeruginosa*), *Neisseria* (e.g., *N. meningitidis*), *Streptococcus* (e.g., *S. pneumoniae*), *Klebsiella* (e.g., *K. oxytoca*), *Salmonella*, *Acinetobacter* (e.g., *A. baumannii*), *Enterobacter* (e.g., *E. cloacae*), *Proteus* (e.g., *P. vulgaris*), *Serratia* (e.g., *S. marcescens*), or *Escherichia* (e.g., *E. coli*)) and diseases in livestock and humans (e.g., acetaldehyde, acetic acid, acetone, acetonitrile, amine, 2-aminoacetophenone, butadiene, 1-butanol, 2-butanone, 1-decanol, dimethyl disulfide, dimethyl sulfide, ethanol, ethylene glycol, formaldehyde, hexanal, hydrogen sulfide, indole, isobutanol, isopentanol, 9-isopentanol, isopentyl acetate, isoprene, methanethiol, methanol, methyl p-anisate, 2-methyl-1-butanol, methyl nicotinate, 4-methylphenol, methyl phenylacetate, 2-nonanone, pentanol (including any isomer thereof), 2-pentanone, o-phenyl anisole, propanol, propene, pyrimidine, toluene, or trimethylamine); pesticides; water contaminants, e.g., trihalomethanes; explosives-related compounds (e.g., 2,3-butanediol, n-decane, dicyclohexylamine, 2,6-dimethylaniline, 2,6-dimethylphenol, 2,3-dimethyl-2,3-dinitrobutane (DMNB), 2-ethyl-hexanoic acid, methyl decanoate, methyl dodecanoate methyl undecanoate, nitrobenzene, 2-nitrotoluene, 3-nitrotoluene, nonanal, 1-octanol, triacetone triperoxide (TATP), or n-undecane); or chemical warfare agents (CWAs), e.g., dimethyl methylphosphonate (DMMP) in any sample (e.g., in soil, water, breath, saliva, food, liquid, milk, etc.), as well as gaseous or GC processed forms of any of these samples.

Two or more sealed μGC columns can be employed for multidimensional GC analysis. Additional uses and analytes are described in Cortes H J et al., "Comprehensive two dimensional gas chromatography review," *J. Sep. Sci.* 2009; 32:883-904; and Seeley J V et al., "Multidimensional gas chromatography: fundamental advances and new applications," *Anal. Chem.* 2013; 85:557-78, each of which is incorporated herein by reference in its entirety.

Components

The sealed μGC column of the application can include any useful component. For instance, the column can be connected fluidically (e.g., by way of tubing or a capillary from the proximal or distal channel or connector region) to a detector, e.g., a mass spectrometry detector, a flame ionization detector, a thermal conductivity detector, an electron-capture detector, an atomic emission detector, a GC chemiluminescence detector, or a photoionization detector, as well as a data analysis device.

In use, the column(s) and its components can be used to separate analytes with a wide range of boiling points, e.g., by raising the temperature of the GC column in a monotonic temperature ramp. Whereas lower temperatures allow more volatile compounds to be released from the column more quickly, higher temperatures increase the rate at which less volatile compounds travel through the column. In this manner, both higher and lower boiling point analytes can be separated and detected. The separated analytes (obtained after traveling through the μGC column) are then transported to the detector for sample identification. Finally, a data analysis device translates the detector signals into a GC chromatogram.

To facilitate heating of the column (e.g., to increase the efficiency or specificity of separation), one or more heating elements can be present. The heating element can include a resistive material, e.g., refractory metal or a doped semiconductor material, such as Pt on an optional adhesive layer. In one embodiment, the heating element is a thermoelectric cooler, such as those having a p-n junction configured to either cool or heat a portion of the column, as well as any described in U.S. Pat. No. 6,706,091, which is incorporated herein by reference in its entirety. The heating element can be used in combination with an insulator (e.g., silicon nitride) disposed between the heating element and the column; a thermistor, such as to monitor the temperature; a heat sink; as well as a control board (e.g., a printed circuit board, a ceramic substrate, such as a low-temperature co-fired ceramic (LTCC) substrate) to provide power and/or electrical signals to the heating element.

The column can also be used with any other component to aid in the detection of one or more analytes. Exemplary components include one or more preconcentrators, such as those described in Lewis P R et al., "Recent advancements in the gas-phase MicroChemLab," *IEEE Sens. J.* 2006 June; 6(3):784-95 or Manginell R P et al., "Mass-sensitive microfabricated chemical preconcentrator," *J. Microelectromech. Sys.* 2008 December; 17(6):1396-407, each of which is incorporated herein by reference in its entirety; microvalves, such as those described in Galambos P et al., "Active MEMS valves for flow control in a high-pressure micro-gas-analyzer," *J. Microelectromech. Sys.* 2011 October; 20(5):1150-62, which is incorporated herein by reference in its entirety; lids; fluidic interconnects or ports, such as those described in U.S. Pat. No. 6,699,392, which is incorporated herein by reference in its entirety; and/or a microhotplate, such as those described in U.S. Pat. No. 8,298,488, which is incorporated herein by reference in its entirety. The column and its components can be provided separately or, alternatively, integrated monolithically, as described in, e.g., Manginell R P et al., "A monolithically-integrated μGC chemical sensor system," *Sensors* 2011; 11:6517-32, which is incorporated herein by reference in its entirety.

Materials

The μGC column can be formed from any useful material. In some instances, the substrate and/or lid is formed from a vapor impermeable material, in which the base material itself is impermeable or a permeable or semi-permeable material is then coated with an impermeable coating material. Exemplary base materials and coating materials include silicon, silica, a glass (e.g., borosilicate glass), a ceramic (e.g., an aluminum oxide), or a polymer (e.g., a cyclic olefin homopolymer or an acrylate). In particular embodiments, the material is vapor impermeable, as well as have a melting temperature above the boiling point of the analyte to be tested. Electrical components (e.g., bond pads, wires, contacts, etc.) can be formed from any useful conductive material, such as a conductive metal or a refractory metal, as well as alloys or layered forms thereof.

Methods of Fabrication

Fabrication steps typically include forming a flow channel (or a portion thereof) in a substrate, aligning the substrate with a lid or a channel layer, bonding the substrate and the lid to form a stack, and then dicing the stack to form a die. Any of these structures can be constructed using any useful method. For instance, flow channels, channels, and connector regions can be defined by etching the substrate, lid, and/or channel layer. Such etching processes include photopatterning one or more channel dimensions, performing a wet etch or plasma etch step, and conducting an optional acid etch step to smooth channel surfaces.

A stack can be formed by aligning and then bonding of two or more layers (e.g., a substrate and a lid), where exemplary bonding methodologies include anodic bonding or cold bonding. Exemplary wet etch and plasma etch methodologies include dry reactive ion etching (DRIE), silicon bulk micromachining, anisotropic etching, Bosch etching, a high-aspect ratio Si etch (HARSE) process, plasma etching, reactive ion etching (RIE, such as with $SF_6$), wet acid etching, wet KOH etching, and/or BOE etching. Alternatively, channel dimensions can be defined by ablating, stripping, or milling the substrate, lid, or channel layer, such as with, e.g., Lithographie, Galvanoformung, Abformung (LiGA), laser milling, or laser ablating; or by molding the base material, such as with hot pressing, printing, or extruding.

Any channel or chamber surface can be further modified. For instance, modifications can include DRIE polymer vapor deposition, chemical vapor deposition (CVD), plasma-enhanced CVD (e.g., for oxide deposition), thermal oxidation, and etching (e.g., electrochemical, oxidation, wet chemical, acid, and/or anisotropic etching).

Other exemplary methods of fabrication include rapid prototyping, microfabrication (e.g., by casting, injection molding, compression molding, embossing, ablation, thin-film deposition, and/or Computer Numerically Controlled (CNC) micromachining), photolithography, etching techniques (e.g., wet chemical etching, reactive ion etching, inductively coupled plasma deep silicon etching, laser ablation, or air abrasion techniques), methods for integrating these structures into high-throughput analysis equipment (e.g., integration with a microplate reader or a control instrument, such as a computer), methods for fabricating and integrating valves (e.g., one or more pneumatic valves or microvalves), and methods for providing vias or inlets (e.g., by piercing, drilling, ablating, or laser cutting), as well as any described in Matzke C M et al., "Microfabricated silicon gas chromatographic micro-channels: fabrication and performance," *Proc. SPIE* 1998; 3511:262-8, which is incorporated herein by reference in its entirety.

Examples

Example 1: High-Yield, Membrane Enhanced Gas Chromatography Columns

The present application provides a μGC design that solves an enduring problem with μGCs constructed using conventional silicon microfabrication techniques. A typical μGC fabrication process etches channels into a silicon substrate, anodically bonds a glass lid to the top of the channels, and then dices the wafer. In this last dicing step, individual dies or devices are separated from the wafer, thereby providing a plurality of dies, where each dies include a column and one or more connection regions. The dicing step also introduces fluid and particulate contaminants into the high-aspect ratio channels. These contaminants, consisting of adhesives, polymers, and particulates made from silicon and glass, are introduced into the channels with the water that is used as a coolant and a lubricant during dicing. Such contaminants can reduce column performance and manufacturability, as well as interfere with column flow and with the deposition of stationary phase chemistries.

Modern μGC designs generally require high aspect ratio channels, many of them with a length-to-width aspect ratio of over 25:1. While such high aspect ratios provide efficient separations, these channels are difficult to clean. Flushing with a variety of alcohols, water, and other solvents removes some contaminants, but the laminar flow within the channels provides insufficient force to remove them all. While alternate techniques to remove individual die from the wafer exist, such as laser cutting and scribe and break processes, the thickness of the glass-silicon stack for modern μGC devices (~1.5 mm) precludes their use.

Figure 5A:
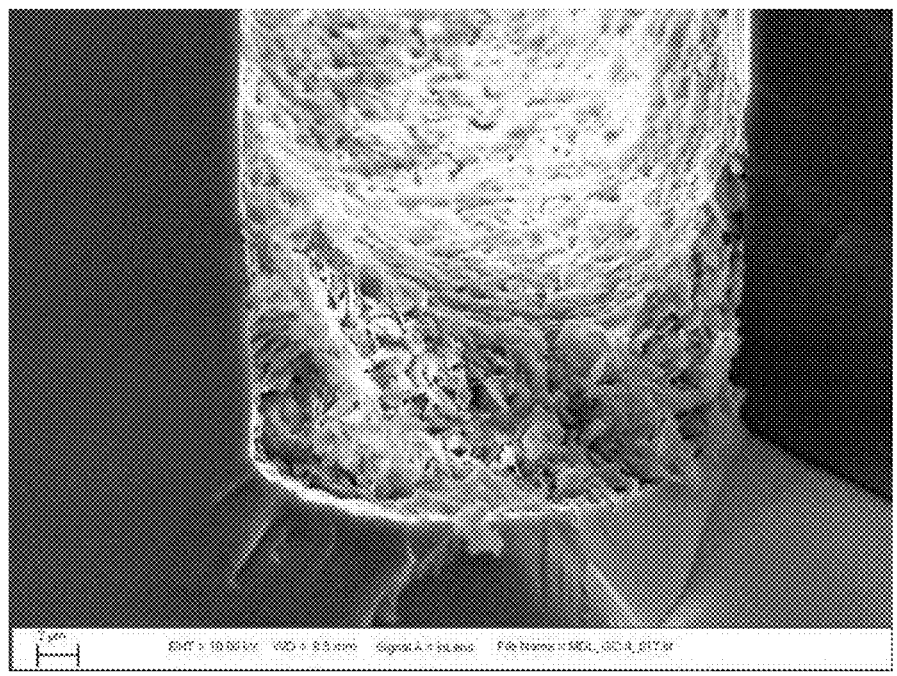
FIG. 5A-5B provides scanning electron micrographs of μGC columns formed (A) without the sealed structure, showing the presence of contaminants, and (B) with the sealed structure.
Figure 5B:
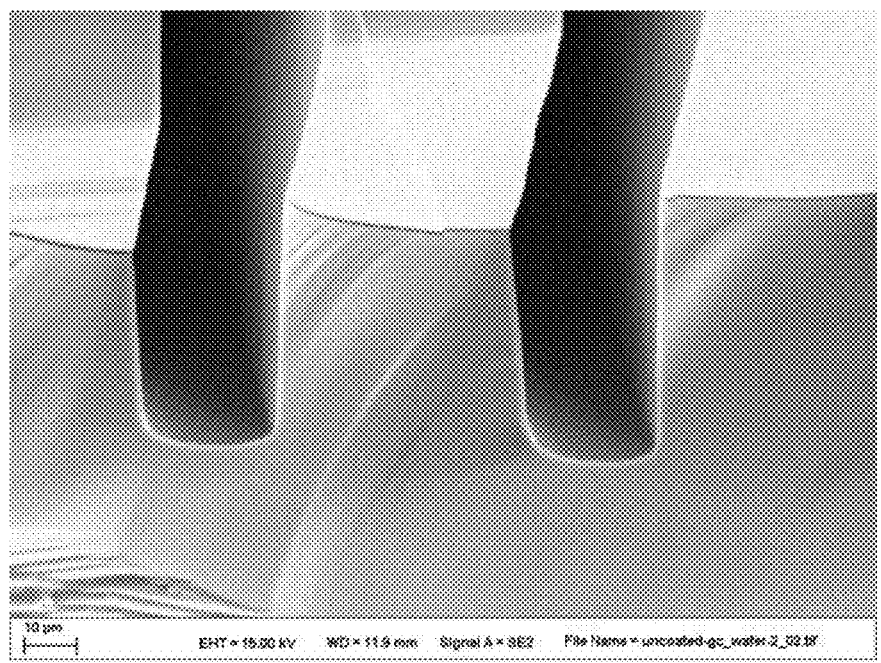

To solve this problem, we have engineered thin membrane sealing structures into the design of our new μGC s. These seals are only broken in a clean environment immediately before fluidic connections are made to the chip, leaving a pristine column surface for deposition of the μGC stationary phase chemistries. The temporary membrane structures can be of any useful dimension, e.g., of ~100 μm thickness, at the inlets of the μGC columns. These structures seal the channels and fluid connections, preventing water and dicing debris from entering the μGC. After dicing and cleaning of the chip exterior, a probe tip or other mechanical tool can be used to rupture the membrane, allowing the μGC fluidic connections to be made. For instance, FIG. 5A shows an SEM image of debris present in a μGC column when seals are not used. In contrast, a pristine surface is provided when a sealed μGC column is employed during the dicing process (FIG. 5B). The membrane rupture produces a minor amount of silicon particulate in the fluidic connectors, but these loose particles are easily removed via a vacuum line. Furthermore, sealed columns can also be stored for long periods of time without fear of atmospheric contaminants entering the channels. This allows relatively large volume manufacturing of μGC parts to take place without compromising their long-term cleanliness during storage.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A sealed, microfabricated gas chromatography column comprising:
   a flow channel disposed within a substrate;
   a proximal connector region and a distal connector region, wherein each connector region is in fluidic communication to the flow channel; and
   a proximal seal disposed in the proximal connector region and a distal seal disposed in the distal connector region, wherein each seal comprises a dimension ranging from about 10 µm to about 500 µm, and wherein each seal is configured to be ruptured mechanically.

2. The sealed column of claim 1, further comprising a lid disposed beneath the substrate, wherein a surface of the flow channel comprises a surface, or a portion thereof, of the lid.

3. The sealed column of claim 2, wherein a height h of the substrate and the lid ranges from about 1 mm to about 10 mm.

4. The sealed column of claim 1, wherein each seal and the substrate are formed from the same base material.

5. The sealed column of claim 4, wherein the base material comprises silicon or glass.

6. The sealed column of claim 1, wherein each seal comprises a length $l_s$, wherein $l_s$ from about 10 to about 500 µm.

7. The sealed column of claim 6, wherein the flow channel has a ratio of a height $h_f$ to a width $w_f$ of more than about 25:1.

8. The sealed column of claim 6, wherein $l_s$ is of from about 50 µm to about 250 µm.

9. A device comprising:
   a sealed column of claim 1, wherein the sealed column has a top surface and a bottom surface;
   a heating element disposed above the top surface of the sealed column; and
   a lid disposed beneath the bottom surface of the sealed column.

10. The device of claim 9, further comprising an insulator disposed between the sealed column and the heating element.

11. The device of claim 10, further comprising a control board disposed beneath the lid, wherein the control board is connected electrically to the heating element.

12. A sealed, microfabricated gas chromatography column comprising:
   a flow channel disposed within a substrate;
   a proximal connector region and a distal connector region, wherein each connector region is disposed in the substrate and wherein each region is in fluidic communication to the flow channel;
   a lid disposed beneath the substrate, wherein a surface of the flow channel comprises a surface, or a portion thereof, of the lid;
   a proximal channel and a distal channel, wherein each proximal and distal channel is disposed in the lid and wherein each proximal and distal channel is in fluidic communication to the flow channel; and
   a proximal seal disposed in the proximal channel and a distal seal disposed in the distal channel, wherein each seal comprises a dimension ranges from about 10 µm to about 500 µm, and wherein each seal is configured to be ruptured mechanically.

13. The sealed column of claim 12, wherein a height H of the substrate and the lid is of from about 1 mm to about 10 mm.

14. The sealed column of claim 12, wherein each seal and the substrate are formed from the same base material.

15. The sealed column of claim 14, wherein the base material is silicon or glass.

16. The sealed column of claim 12, wherein each seal comprises a length $l_s$ of from about 10 to about 500 µm.

17. The sealed column of claim 16, wherein the flow channel has a ratio of a height $h_f$ to a width $w_f$ of more than about 25:1.

18. The sealed column of claim 16, wherein $l_s$ is of from about 50 µm to about 250 µm.

19. A method of fabricating a sealed, microfabricated gas chromatography column, the method comprising:
   providing a substrate comprising a flow channel, wherein the substrate comprises a top surface and a bottom surface;
   bonding a channel layer and/or a lid to the bottom surface of the substrate, thereby forming a stack; and
   dicing the stack in the presence of a lubricant and/or a coolant, wherein said dicing step comprises employing a dice line located a length $l_s$ from the edge of the stack, wherein $l_s$ ranges from about 10 to about 500 µm, thereby providing at least one seal along the dice line.

20. The method of claim 19, wherein the substrate further comprises a proximal connector region and a distal connector region, and wherein each connector region is in fluidic communication to the flow channel.

21. The method of claim 20, wherein the length $l_s$ is between the edge of the stack and a surface of one of the connector regions, thereby providing a seal disposed in at least one connector region.

22. The method of claim 19, wherein the length $l_s$ is between the edge of the stack and a surface of the flow channel, thereby providing a seal disposed in the flow channel.

23. The method of claim 19, wherein the stack comprises the substrate, the channel layer disposed beneath the substrate, and the lid disposed beneath the channel layer.

24. The method of claim 23, wherein the channel layer comprises a proximal channel and a distal channel, and wherein each proximal and distal channel is in fluidic communication to the flow channel.

25. The method of claim 24, wherein the length $l_s$ is between the edge of the stack and a surface of the proximal and/or distal channel, thereby providing a seal disposed in the proximal and/or distal channel.

26. The method of claim 19, wherein the stack comprises the substrate and the lid disposed beneath the substrate.

27. The method of claim 26, wherein the lid comprises a proximal channel and a distal channel, and wherein each proximal and distal channel is in fluidic communication to the flow channel.

28. The method of claim 19, wherein the flow channel has a ratio of a height $h_f$ to a width $w_f$ of more than about 25:1.

29. The method of claim 19, further comprising rupturing mechanically the seal, thereby providing an unsealed column.

30. The method of claim 29, further comprising coating the flow channel of the unsealed column with a stationary phase.

\* \* \* \* \*